United States Patent
Vora

[11] Patent Number: 6,005,150
[45] Date of Patent: Dec. 21, 1999

[54] PROCESS FOR THE PRODUCTION OF BUTENE-1 FROM A MIXTURE OF C4 OLEFINS

[75] Inventor: Bipin V. Vora, Darien, Ill.

[73] Assignee: UOP LLC, Des Plaines, Ill.

[21] Appl. No.: 09/103,180

[22] Filed: Jun. 22, 1998

[51] Int. Cl.$^6$ .............. C07C 1/00; C07C 41/06
[52] U.S. Cl. .......... 585/324; 585/326; 585/327; 585/329; 568/697
[58] Field of Search .............. 585/324, 326, 585/327, 329; 568/697

[56] References Cited

U.S. PATENT DOCUMENTS

| | | | |
|---|---|---|---|
| 2,537,283 | 1/1951 | Schaad | 260/683.2 |
| 3,211,801 | 10/1965 | Holm et al. | 260/683.2 |
| 3,270,085 | 8/1966 | Noddings et al. | 260/683.2 |
| 3,304,343 | 2/1967 | Mitustani | 260/683.2 |
| 3,327,014 | 6/1967 | Noddings | 260/683.2 |
| 3,448,164 | 6/1969 | Holm et al. | 260/683.2 |
| 3,723,564 | 3/1973 | Tidwell et al. | 260/683.2 |
| 3,751,502 | 8/1973 | Hayes et al. | 260/668 A |
| 3,800,003 | 3/1974 | Sobel | 260/683.49 |
| 3,972,832 | 8/1976 | Butter et al. | 252/437 |
| 4,232,177 | 11/1980 | Smith, Jr. | 585/324 |
| 4,423,264 | 12/1983 | Juguin et al. | 585/255 |
| 4,482,775 | 11/1984 | Smith, Jr. | 585/671 |
| 4,593,146 | 6/1986 | Johnson et al. | 585/667 |
| 4,797,133 | 1/1989 | Pujado | 44/53 |
| 5,210,327 | 5/1993 | Luebke et al. | 568/697 |
| 5,221,441 | 6/1993 | Smith, Jr. | 568/697 |
| 5,258,560 | 11/1993 | Marker | 568/697 |
| 5,292,984 | 3/1994 | Gajda et al. | 585/667 |
| 5,395,981 | 3/1995 | Marker | 568/697 |
| 5,491,267 | 2/1996 | Frey et al. | 568/697 |
| 5,523,502 | 6/1996 | Rubin | 585/324 |
| 5,550,300 | 8/1996 | Taylor, Jr. et al. | 568/698 |
| 5,563,299 | 10/1996 | Paludetto et al. | 568/697 |
| 5,672,771 | 9/1997 | Trotta et al. | 568/697 |
| 5,792,891 | 8/1998 | Adams et al. | 568/697 |

*Primary Examiner*—Walter D. Griffin
*Attorney, Agent, or Firm*—Thomas K. McBride; John G. Tolomei; Richard P. Silverman

[57] ABSTRACT

A simplified process for jointly producing butene-1 and ether in a catalytic distillation zone which comprises an upper catalytic zone for etherification and a lower catalytic zone for isomerization of $C_4$ plus olefins. The process is especially usefull when combined with a process for the production of light olefins including ethylene and propylene from methanol. According to the invention, the produced butene-1 stream is combined with ethylene to produce polyethylene.

21 Claims, 2 Drawing Sheets

PROCESS FOR THE PRODUCTION OF BUTENE-1 FROM A MIXTURE OF C4 OLEFINS

FIELD OF THE INVENTION

This invention relates to an improved process for the conversion of hydrocarbons, and more specifically for the catalytic isomerization of olefinic hydrocarbons.

BACKGROUND OF THE INVENTION

Olefinic hydrocarbons are feedstocks for a variety of commercially important additional reactions to yield fuels, polymers, oxygenates and other chemical products. The specific olefin isomer, considering the position of the double bond or the degree of branching of the hydrocarbon, may be important to the efficiency of the chemical reaction or to the properties of the product. The distribution of isomers in a mixture of olefinic hydrocarbons is rarely optimum for a specific application. It is often desirable to isomerize olefins to increase the output of the desired isomer.

Butenes are among the most useful of the olefinic hydrocarbons having more than one isomer. A high-octane gasoline component is produced from a mixture of butenes in many petroleum refineries principally by alkylation with isobutane; 2-butenes (cis- and trans-) generally are the most desirable isomers for this application. Secondary-butyl alcohol and methylethyl ketone, as well as butadiene, are other important derivatives of 2-butenes. Demand for 1-butene has been growing rapidly based on its use as a co-monomer for linear low-density polyethylene and as a monomer in polybutene production. Isobutene finds application in such products as methyl methacrylate, polyisobutene and butyl rubber. The most important derivative influencing isobutene demand and butene isomer requirements, however, is methyl t-butyl ether (MTBE) which is experiencing rapid growth in demand as a gasoline component. Pentenes also are valuable olefinic feedstocks for fuel and chemical products.

Catalytic isomerization to alter the ratio of isomers is one solution to this need. Since ethers must be supplied at lower cost to find widespread use as a fuel product and since isomerization competes with increased feedstock processing as a source of desired isomers, an isomerization process must be efficient and relatively inexpensive. In one aspect, a catalytic isomerization process must recognize olefin reactivity: isobutene in particular readily forms oligomers which could require a reconversion step to yield monomer if produced in excess. The principal problem facing workers in the art, therefore, is to isomerize olefins to increase the concentration of the desired isomer while minimizing product losses to heavier or lighter products.

U.S. Pat. No. 4,797,133 discloses a process for the recovery of butene-1 from a mixed $C_4$ feed stream which also contains isobutylene, butene-2, isobutane, and normal butane. The $C_4$ feedstream is passed through an etherification zone to selectively convert isobutylene to an ether to produce a first stream comprising the product ether and $C_4$ hydrocarbons and a second stream comprising isobutane and butene-1. The second stream is then separated to yield butene-1. The first stream is alkylated for use in a motor fuel. Butene-2 isomers (cis- and trans-) are desired feedstocks to an alkylation reactor in which the butene-2 isomers react with isobutane to produce alkylate.

U.S. Pat. No. 4,423,264 discloses a process for the production of a pure butene-1 and a premium gasoline from a $C_4$ olefinic hydrocarbon fraction. According to the disclosure, the $C_4$ olefinic hydrocarbon fraction is polymerized and disproportionated to partially convert the isobutene to a gasoline/jet fuel boiling range component (e.g., an isobutene dimer and trimer), hydrogenating the gasoline/jet fuel boiling range fraction to produce a stabilized fuel component, and fractionating the remaining $C_4$ olefins to obtain a high purity butene-1 product.

U.S. Pat. No. 5,523,502 discloses a process for the deep catalytic cracking of petroleum feedstocks to produce a full range of synthetic hydrocarbons including a $C_4$ hydrocarbon fraction which includes $C_4$ paraffins and butenes. In processing the $C_4$ hydrocarbon fraction, combinations of separate processing includes: hydroisomerization of butene-1 to butene-2, butadiene hydrogenation, and etherification. The remaining butenes are passed to an extractive distillation process to separate the olefins (butene-1 and butene-2) from any paraffins (normal butane, etc.), and the olefins are passed to a skeletal isomerization unit and therein converted to isobutene which is recycled to the etherification zone to produce more MTBE.

Processes for the isomerization of olefinic hydrocarbons are widely known in the art. Many of these use catalysts comprising phosphate. U.S. Pat. No. 2,537,283 (Schaad), for example, teaches an isomerization process using an ammonium phosphate catalyst and discloses examples of butene and pentene isomerization. U.S. Pat. No. 3,211,801 (Holm et al.) discloses a method of preparing a catalyst comprising precipitated aluminum phosphate within a silica gel network and the use of this catalyst in the isomerization of butene-1 to butene-2. U.S. Pat. Nos. 3,270,085 and 3,327,014 (Noddings et al.) teach an olefin isomerization process using a chromium-nickel phosphate catalyst, effective for isomerizing 1-butene and higher alpha-olefins. U.S. Pat. No. 3,304,343 (Mitsutani) reveals a process for double-bond transfer based on a catalyst of solid phosphoric acid on silica, and demonstrates effective results in isomerizing 1-butene to 2-butenes. U.S. Pat. No. 3,448,164 (Holm et al.) teaches skeletal isomerization of olefins to yield branched isomers using a catalyst containing aluminum phosphate and titanium compounds. U.S. Pat. No. 4,593,146 teaches isomerization of an aliphatic olefin, preferably 1-butene, with a catalyst consisting essentially of chromium and amorphous aluminum phosphate. None of the above references disclose the olefin-isomerization process using the non-zeolitic molecular sieve (NZMS).

The art also contains references to the related use of zeolitic molecular sieves. U.S. Pat. No. 3,723,564 (Tidwell et al.) teaches the isomerization of 1-butene to 2-butene using a zeolitic molecular sieve. U.S. Pat. No. 3,751,502 (Hayes et al.) discloses the isomerization of mono-olefins based on a catalyst comprising crystalline aluminosilicate in an alumina carrier with platinum-group and Group IV-A metallic components. U.S. Pat. No. 3,800,003 (Sobel) discloses the employment of a zeolite catalyst for butene isomerization. U.S. Pat. No. 3,972,832 (Butler et al.) teaches the use of a phosphorus-containing zeolite for butene conversion in which the phosphorus has not been substituted for silicon or aluminum in the zeolite framework. U.S. Pat. No. 5,292,984 discloses the use of a non-zeolitic molecular sieve, NZMS, for the isomerization of pentenes in a pentene-containing feedstock comprising a raffinate from an etherification process. U.S. Pat. No. 5,292,984, which is hereby incorporated by reference, discloses the use of a catalyst comprising at least one NZMS and having the absence of a platinum-group metal demonstrates surprising efficiency in converting butene-2 to isobutene or butene-1 in a butene isomerization operation and in the skeletal isomerization of pentenes.

Efficient production of butene-1 has remained a problem in the art, requiring complex, multi-step processes to recover butene-1, often as a by-product of motor fuel production. In such processes, the objective is butene-2 which can be alkylated to produce a high octane, low vapor pressure product. Often when butene-1 is isolated, it is further skeletally isomerized to produce more isobutene.

It is the objective of the present invention to provide a simplified process for the recovery of butene-1 from $C_4$ olefin streams. It is a further objective of the present invention to provide a reduced cost process for selectively and directly producing butene-1 from $C_4$ olefinic hydrocarbon streams.

SUMMARY OF THE INVENTION

This invention provides a novel, simplified process for the production of butene-1 from a $C_4$ olefin stream consisting of isobutene, butene-1, butene-2, butadiene, and pentenes. Such streams are generally derived from methanol-to-olefin processes which convert methanol, dimethyl ether and the like to light olefins. The light olefin streams produced in this manner have very small amounts of paraffin components in any single carbon number group and consist essentially of ethylene, propylene, butenes and pentenes, with less than 1–5 mol-% paraffins produced in any single carbon range. The invention is based on the integration of etherification and butene isomerization into a single catalytic distillation zone wherein the isobutene is reacted with an alcohol such as methanol to produce a tertiary alkyl ether and the remaining butenes are selectively isomerized in the presence of hydrogen to butene-1. The hydrogen is introduced to the catalytic distillation zone by injecting hydrogen into a liquid side draw stream and returning the hydrogen admixture directly to the isomerization zone to avoid hydrogen distribution problems. Butene-1 and unreacted methanol are withdrawn from the upper section of the catalytic distillation zone. The invention is based on the recognition of the synergy in making the combination in a single catalytic distillation zone. In one embodiment, the single catalytic distillation zone comprises an external isomerization reaction zone in fluid communication with the single catalytic distillation column. The ether is withdrawn from the bottom of the catalytic distillation zone along with any dimer formed by the contact of butadiene with the isomerization catalyst. In an alternate embodiment, a selective hydrogenation catalyst can be combined with the isomerization catalyst to increase the yield of butene-1. Following the removal of the oxygenate from the butene-1, the butene-1 can be withdrawn as a finished product or polymerized with ethylene to produce polyethylene.

In one embodiment, the invention is a process for the production of butene-1 from a feedstream comprising butene-1, butene-2, isobutylene, and pentenes. The process comprises a series of steps. The feedstream and an alcohol stream at effective separation and etherification conditions is passed to a catalytic distillation zone having an upper catalytic zone and a lower catalytic zone. In the catalytic distillation zone at least a portion of the feedstream is contacted in the upper catalytic zone which contains an etherification catalyst. In the upper catalytic zone the isobutylene is etherified with the alcohol stream to produce a tertiary alkyl ether. The remaining portion of the feedstream in the presence of hydrogen and at effective isomerization conditions is contacted in the lower catalytic zone. The lower catalytic zone contains an isomerization catalyst for the isomerization of butene-2 to butene-1 to produce an additional amount of butene-1. A bottoms product stream comprising pentenes and tertiary alkyl ether is recovered from the catalytic distillation zone. A top stream is recovered from the catalytic distillation zone comprising hydrogen. A side draw stream comprising alcohol and butene-1 is withdrawn at a point above the upper catalytic zone. The side draw stream is passed to an alcohol recovery zone to provide a butene-1 product stream and an oxygenate stream; and at least a portion of the oxygenate stream is returned to the catalytic distillation zone to provide at least a portion of the alcohol stream.

In another embodiment, the invention is a process for the production of light olefins comprising ethylene, propylene, and butylene from the conversion of oxygenates. The process comprises a series of steps. At least a portion of an oxygenate feedstream comprising methanol or ethanol in the presence of a diluent at effective conditions is passed to an oxygenate conversion zone containing a SAPO catalyst to produce a reactor effluent stream comprising said light olefins. The reactor effluent stream is passed to a separation zone to produce an ethylene stream, a propylene stream, and a butylene stream. A portion of the oxygenate feedstream is admixed with at least a portion of the butylene stream comprising isobutylene, butene-1, and butene-2 to provide a feed admixture. The feed admixture at effective etherification conditions is passed to a catalytic distillation column having an upper catalytic zone. At least a portion of the feed admixture is contacted in the upper catalytic zone containing an etherification catalyst and therein the isobutylene is etherified with the oxygenate to produce a tertiary alkyl ether. The remaining portion of the feed admixture in the presence of hydrogen and at effective isomerization conditions is contacted in a lower catalytic zone containing an isomerization catalyst for the isomerization of butene-2 to butene-1 to produce an additional amount of butene-1. A bottoms product stream comprising the tertiary alkyl ether is recovered from the catalytic distillation column. A top stream is recovered from the catalytic distillation column comprising hydrogen, and a side draw stream is withdrawn at a point above the upper catalytic zone. The side draw stream comprises methanol and butene-1 and is passed to a methanol recovery zone to provide a butene-1 product stream and an oxygenate stream. At least a portion of the oxygenate stream is returned to the oxygenate conversion zone.

DETAILED DESCRIPTION OF THE INVENTION

Figure 1:
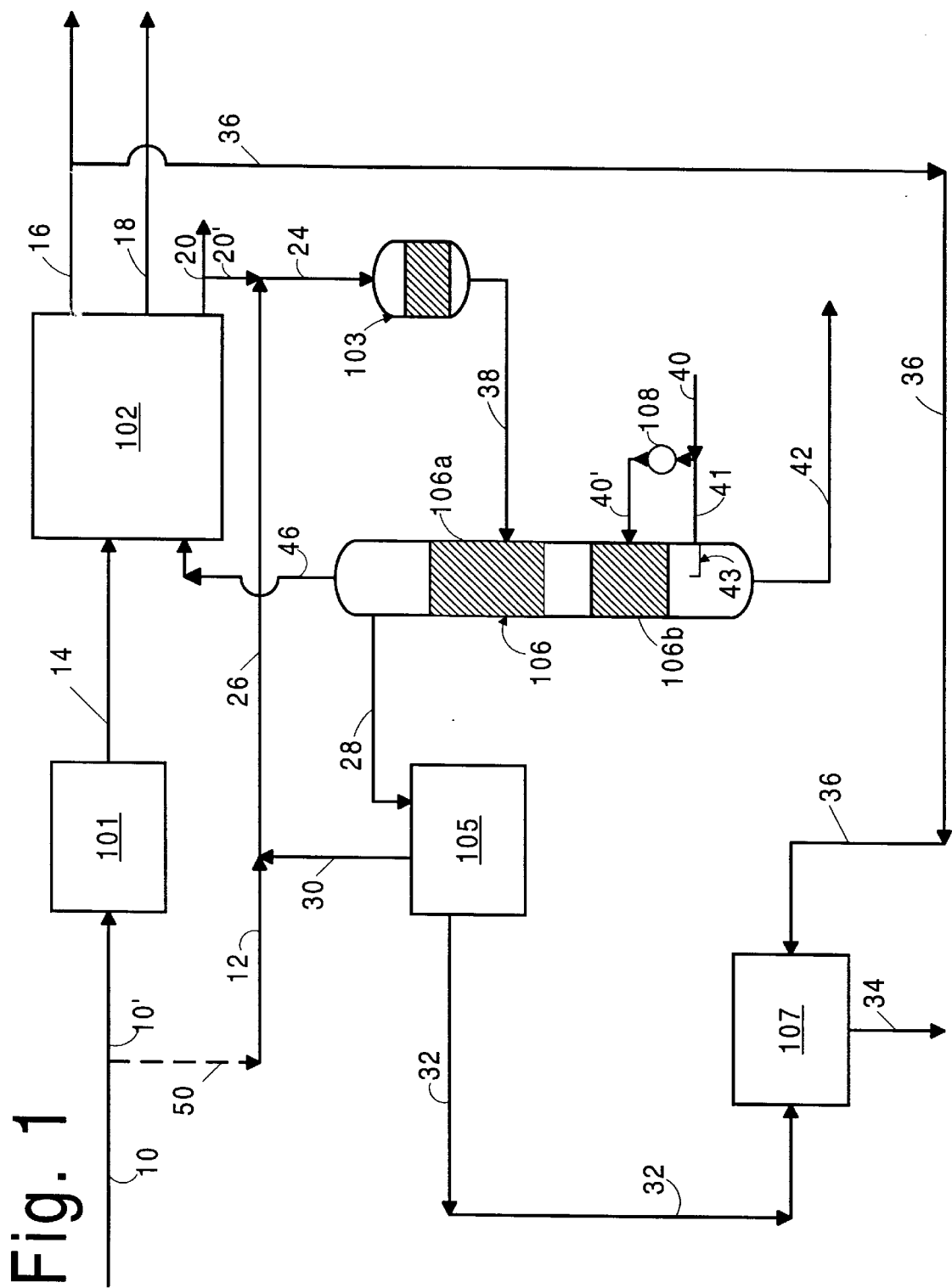
FIG. 1 is a schematic block flow diagram of the process of the present invention.

In the group of olefinic hydrocarbons suitable as feedstock to the catalytic isomerization process of the present invention, mono-olefins having from 4 to 10 carbon atoms per molecule are preferred. The mono-olefins should be present in the feedstock in a concentration of from about 0.5 to 100 wt-%, and preferably from about 5 to 100 wt-%, with most of the balance usually comprising paraffins. Butenes are an especially preferred feedstock. The feedstock should be rich in one or more of the linear butenes, i.e., 1-butene, cis-2-butene and trans-2-butene, if isobutene is the desired product.

The feedstock olefins may be contained in product streams from petroleum-refining, synthetic-fuel, or petrochemical operations such as catalytic cracking, thermal cracking, stream pyrolysis, oligomerization, and Fischer-Tropsch synthesis. Often the feedstock contains paraffins such as butanes, pentanes, and $C_6$ and higher paraffins. An advantageous feedstock for isobutene or isopentene production is raffinate from an etherification process. The derivation of the feedstock from an etherification process is well known and is described, inter alia, in a paper by Bruno Notari, et al., "Skeletal Isomerization of Olefins," at the 1980 NPRA Annual Meeting in New Orleans on Mar. 23–25, 1980. These streams may require removal of polar contaminants such as sulfur, nitrogen or oxygen compounds by, e.g., extraction or adsorption to maintain isomerization-catalyst stability. Raffinate from an etherification process would beneficially be water-washed to remove methanol and other oxygenates present at levels which could affect the performance of the present catalyst. Removal of dienes and acetylenes, e.g., by selective hydrogenation or polymerization, also may be desirable.

A detailed description of processes for the production of MTBE from iso-butylene and methanol, including catalyst, processing conditions, and product recovery, are provided in U.S. Pat. Nos. 2,720,547 and 4,219,678 and in an article at page 35 of the Jun. 25, 1979 edition of Chemical and Engineering News. The preferred process is described in a paper presented at The American Institute of Chemical Engineers, 85th National Meeting on Jun. 4–8, 1978, by F. Obenaus et al. The above references are herein incorporated by reference. Other etherification processes of interest are the production of tertiary amyl methyl ether (TAME) by reacting $C_5$ iso-olefins with methanol; the production of ethyl tertiary butyl ether (ETBE) by reacting $C_4$ iso-olefins with ethanol; the production of tertiary amyl ethyl ether (TAEE) by reacting $C_5$ iso-olefins with ethanol; and, the production of tertiary hexyl methyl ether (THME) by reacting $C_6$ iso-olefins with methanol. Etherification reactions are carried out in the presence of an acid catalyst such as a sulfonated, macroporous organic ion exchange resin in the liquid phase at temperatures between about 30 and about 100° C.

Generally, the production of ethylene is accompanied by the production of di-olefins such as butadiene. These di-olefins are typically removed prior to the production of any ethers or prior to introducing the butene and heavier stream to the butene cracking reactor. Butadiene produced in ethylene plants by the steam cracking process is present in amounts which often justify the recovery of the butadiene by extractive distillation or solvent extraction. U.S. Pat. Nos. 4,038,156 and 4,128,457, hereby incorporated by reference, disclose the use of a polar solvent such as acetonitrile to recover butadiene by extractive distillation. When $C_4$ plus olefins are produced in fluid catalytic cracking and methanol to olefins processes, the concentration of butadiene is significantly smaller than when they are produced by steam cracking. Butadiene found in such streams is generally removed by selective hydrogenation in the presence of a solid catalyst comprising nickel and a noble metal such as platinum or palladium or silver as disclosed in U.S. Pat. No. 4,409,410, hereby incorporated by reference.

Processes for the isomerization are carried out at effective isomerization conditions including reaction temperatures generally in the range of about 50° to 750° C. Selective butene isomerization to produce 1-butene is effected preferably at temperatures of from 50° to 300° C. Pentene isomerization is advantageously performed at temperatures in the range of about 200° to 500° C. Isomerization reactor operating pressures usually will range from about atmospheric to 50 atmospheres. The amount of catalyst in the reactors will provide an overall weight hourly space velocity of from about 0.5 to 100 $hr^{-1}$, and preferably the overall weight hourly space velocity will comprise from about 1 to 40 $hr^{-1}$.

The catalytic distillation column of the present invention is carried out at effective separation conditions which include a separation temperature ranging from about 30° C. to about 500° C. and a pressure of between atmospheric to about 50 atmospheres. More preferably, the effective separation conditions of the present invention include a separation temperature ranging from about 30° C. to about 300° C. and a separation pressure ranging from about atmospheric to about 40 atmospheres.

According to the present invention, the butadiene can be employed to produce additional amounts of butene-1 by incorporating the selective hydrogenation catalyst as described hereinabove in the lower catalyst zone of the catalytic distillation zone. In the lower catalytic zone the butadiene is contacted with the selective hydrogenation zone to produce additional butenes such as butene-1 and butene-2. As described hereinabove, the additional butenes are further converted to butene-1 in the bottom catalytic zone. The selective hydrogenation catalyst may be disposed as a separate catalyst bed within the lower catalyst zone or may be admixed with the isomerization catalyst in the lower catalytic zone. Preferably, the ratio of the weight of selective hydrogenation catalyst to the weight of isomerization catalyst will range from about 1 to about 100 and from about 100 to about 1.

In an alternate embodiment, the butadiene in the feedstream can be employed to produce additional motor fuel components as a dimer component. When butadiene is present in the feedstream to the catalytic distillation, the butadiene is passed to the lower catalytic zone and therein is converted to a dimer component which is recovered with the bottom product stream from the catalytic distillation zone. The dimer component has enhanced motor fuel properties such as reduced vapor pressure and improved octane number over the butadiene and may be blended into motor fuel with the tertiary alkyl ether.

DETAILED DESCRIPTION OF THE DRAWINGS

The process of the present invention is hereinafter described with reference to the figures which illustrate various aspects of the present invention. It is to be understood that no limitation to the scope of the claims which follow is intended by the following description. Those skilled in the art will recognize that these process flow diagrams have been simplified by the elimination of many necessary pieces of process equipment including valves, some heat exchangers, process control systems, pumps, fractionation column overhead and reboiler systems, etc. It may also be readily discerned that the process flow presented in the drawings may be modified in many aspects without departing from the basic overall concept of the invention.

Referring to FIG. 1, a feedstream in line 10 is passed to an oxygenate conversion zone 101 via lines 10 and 10'. In the oxygenate conversion zone 101, the oxygenate feedstream in the presence of a diluent is converted to light olefins. A reactor effluent stream comprising ethylene, propylene, butylene, and pentenes is withdrawn from the oxygenate conversion zone 101 and passed in line 14 to a separation zone 102. In separation zone 102 the light olefins are separated in the conventional manner to produce an ethylene stream in line 16, a propylene stream in line 18, and a butylene stream comprising butylene and pentenes in line 20. The propylene stream is withdrawn as a propylene product stream.

At least a portion of the butylene stream in lines 20 and 20' comprising isobutenes, butene-1, and butene-2 is admixed with a portion of the feedstream 10 via lines 10, 50, 12, and 26 to produce a feed admixture in line 24. The feed admixture 24 at effective etherification conditions is passed to a first reaction zone 103, or pre-etherification reactor, containing an etherification catalyst to at least partially convert a portion of the feed admixture into a tertiary alkyl ether and to produce a pre-reactor effluent stream in line 38. The pre-reactor effluent stream is passed to a catalytic distillation zone 106. The catalytic distillation zone 106 contains an upper catalytic zone 106a located at a point in the catalytic distillation zone at or about the entry point of the feed and a lower catalytic zone 106b located at a point in the catalytic distillation zone 106 below the entry point of the feed to the catalytic distillation zone 106. The isobutenes at effective etherification conditions react in the upper catalytic zone 106a to produce additional amounts of tertiary alkyl ether and the butene-2 reacts in the lower catalytic zone 106b to produce butene-1 in the presence of hydrogen which is supplied via line 40. One means of providing hydrogen to the lower catalytic zone 106b is shown in FIG. 1. A liquid draw tray, or trap tray, 43 located below the lower catalytic zone 106b collects a liquid side draw stream comprising butene-2. Preferably, liquid draw tray is located at a point in the catalytic distillation zone 106 where the concentration of butene-2 will be near a maximum concentration. Preferably, the liquid draw tray 43 will be located between 5 and 15 theoretical trays above the bottom of the catalytic distillation zone 106, and more preferably, the liquid draw tray is located at a point 8 to 12 theoretical trays above the bottom of the catalytic distillation zone 106. A butene-2 stream in line 41 comprising butene-2 is withdrawn from the catalytic distillation zone 106 at the liquid side draw tray 43. The butene-2 stream is admixed with hydrogen in line 40 to provide a hydrogen admixture and the hydrogen admixture is passed to pump 108 to provide a lower catalytic zone feed stream in line 40' comprising butene-2 and hydrogen. It is believed that at least a portion of the hydrogen will be in solution in the lower catalytic zone feed stream in line 40'. Because the butene-2 stream was withdrawn at a point below the lower catalytic zone 106b it will have a higher boiling point than the liquids in the catalytic distillation zone within or near the top of the lower catalytic zone 106b. When the butene-2 stream is returned to the catalytic distillation zone 106 at a point within or above the lower catalytic distillation, it is believed that at least a portion of the butene-2, in the presence of hydrogen will be contacted at effective isomerization conditions with the isomerization catalyst in the lower catalytic zone 106b. Thus, it is preferred that lower catalytic feed stream 40' is introduced into the lower catalytic zone at a point below the top of the lower catalytic zone 106b, and more preferably, the lower catalytic feed stream is introduced at a point within the lower catalytic zone 106b. A bottom product stream in line 42 comprising the tertiary alkyl ether and pentenes is withdrawn from the catalytic distillation zone 106. The bottom product stream in line 42 comprising ethers produced in the upper catalytic zone 106a and $C_4$ plus olefins such as pentenes may be employed in gasoline blending as a high octane component of motor fuel. A top product stream is withdrawn from the catalytic distillation zone 106 in line 46. The top product stream comprises hydrogen and light hydrocarbons such as methane through isobutane. The top product stream is returned to the separation zone 102 for removal from the process as a fuel stream (not shown). A second side draw stream is withdrawn from a point in the catalytic distillation zone 106 above the upper catalytic zone 106a in line 28. The second side draw stream comprises unreacted oxygenate and butene-1 and is passed to an oxygenate removal zone 105 wherein the oxygenates such as methanol, ethanol, or propanol are separated in the conventional manner from the butene-1 to provide a butene-1 stream in line 32 and an oxygenate stream in line 30. The oxygenate stream in line 30 is recycled to the catalytic distillation zone 106 by passing the oxygenate stream in lines 30 and 26 to be admixed with the butenes stream in line 20' to form the feed admixture in line 24. The feed admixture in line 24 is passed to the pre-etherification reactor 103 and the pre-reactor effluent is passed to the catalytic distillation column 106.

A portion of the ethylene stream in line 16 is passed via line 36 to a polymerization zone 107 containing a polymerization catalyst wherein butene-1 in line 32 and ethylene in line 36 is polymerized at effective conditions to form a polyethylene product stream in line 34. The polyethylene product comprises a linear low density polyethylene.

Figure 2:
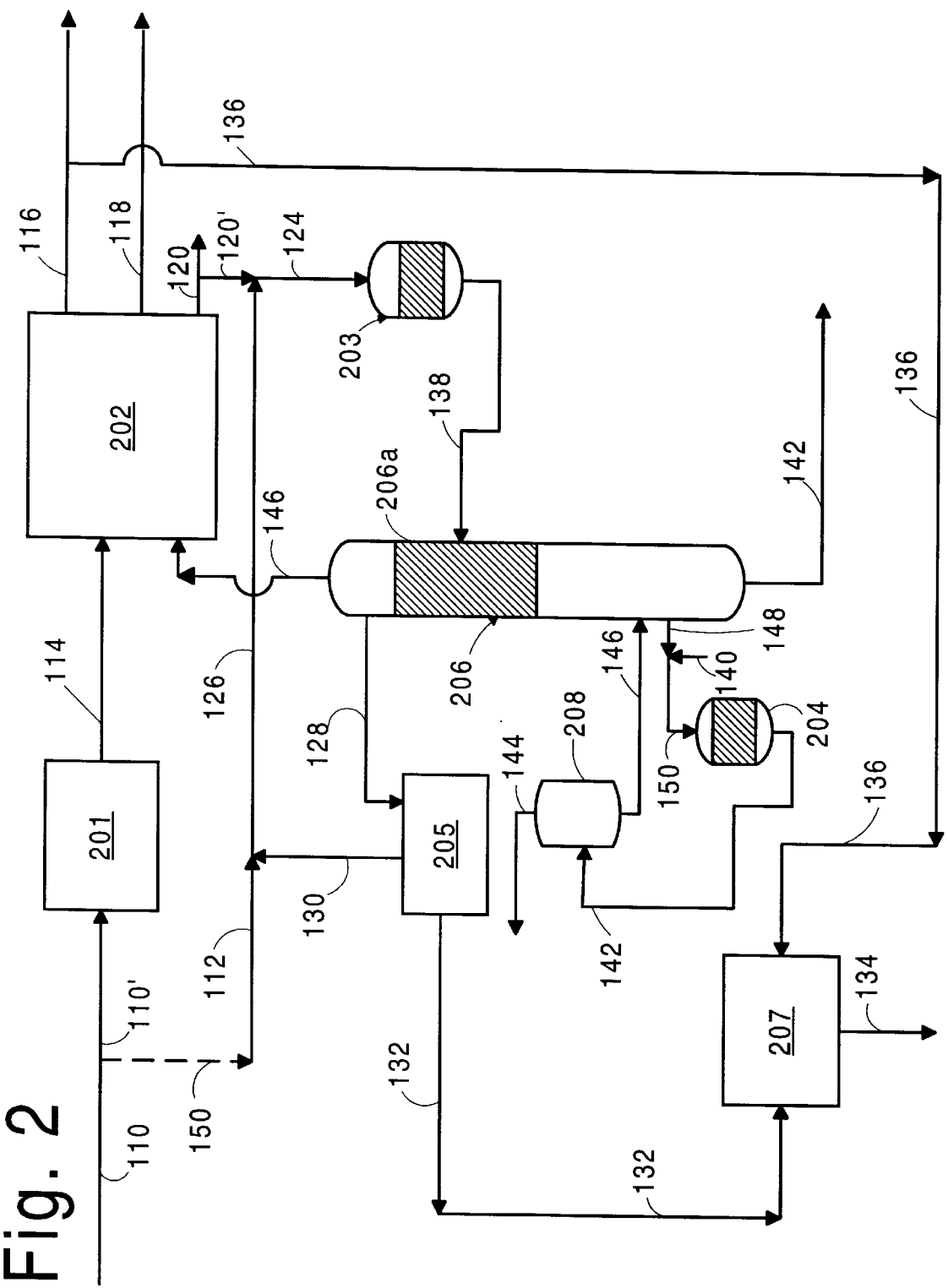
FIG. 2 is a schematic block flow diagram of the process of the present invention with an external isomerization reactor.

In another embodiment, the catalytic distillation zone includes the catalytic distillation column and an external isomerization zone, or lower catalytic zone. A portion of butene isomerization may take place outside of the catalytic distillation column in the lower catalytic zone which is in fluid communication with the catalytic distillation zone. With this option, the hydrogen addition and, optionally, the subsequent stripping of the isomerization reactor effluent is conducted outside of the catalytic distillation column and the isomerization reactor effluent is returned to the catalytic distillation column. Referring to FIG. 2, a feedstream in line 110 is passed to an oxygenate conversion zone 201 via lines 110 and 110'. In the oxygenate conversion zone 201, the oxygenate feedstream in the presence of a diluent at effective oxygenate conversion conditions is converted to light olefins. A reactor effluent stream comprising ethylene, propylene, butylene, and pentenes is withdrawn from the oxygenate conversion zone 201 and passed in line 114 to a separation zone 202. In separation zone 202 the light olefins are separated in a conventional manner to produce an ethylene stream in line 116, a propylene stream in line 118, and a butylene stream comprising butylene and pentenes in line 120. The propylene stream is withdrawn as a propylene product stream in line 118.

At least a portion of the butylene stream in lines 120 and 120' comprising isobutenes, butene-1, and butene-2 is admixed with a portion of the feedstream 110 via lines 110, 150, 112, and 126 to produce a feed admixture in line 124. The feed admixture 124 at effective etherification conditions is passed to a first reaction zone 203 or pre-etherification reactor containing an etherification catalyst to at least partially convert a portion of the feed admixture into a tertiary alkyl ether and to produce a pre-reactor effluent stream in line 138. The pre-reactor effluent stream is passed to a catalytic distillation column 206. The catalytic distillation zone 206 contains an upper catalytic zone 206a located at a point in the catalytic distillation zone above the entry point of the feedstream and a lower catalytic zone 204, a portion of which is located outside of the catalytic distillation column 206. In the catalytic distillation column 206, the iso-butene reacts at effective conditions with oxygenate in the upper catalytic zone 206a to produce additional amounts of tertiary alkyl ether. A top product stream is withdrawn from the catalytic distillation zone 206 in line 146. The top product stream comprises hydrogen and light hydrocarbons such as methane. The top product stream is returned to the separation zone 202 for removal from the process as a fuel stream (not shown). A first side draw stream is withdrawn from a point in the catalytic distillation column 206 above the upper catalytic zone 206a in line 128. The first side draw stream comprises unreacted oxygenate and butene-1 and is passed to an oxygenate removal zone 205 wherein the oxygenates are separated from the butene-1 in the conventional manner to provide a butene-1 stream in line 132 and an oxygenate stream in line 130. The oxygenate stream in line 130 is recycled to the catalytic distillation zone by passing the oxygenate stream in lines 130 and 126 to be admixed with the butenes stream in line 120. A second side draw stream is withdrawn from the catalytic distillation zone 206 at a point below the feed point (where line 138 enters the catalytic distillation column) and passed at effective isomerization conditions in line 148 and line 150 to an isomerization zone 204, or lower catalytic zone. Hydrogen is injected into the second side draw stream via line 140 to provide the presence of hydrogen in the isomerization zone 204. The isomerization zone 204 contains an isomerization catalyst which is selective for the isomerization of butene-2 to butene-1. An isomerization effluent stream in line 142 is withdrawn from the isomerization zone 204 and passed to an optional stripping zone 208 for the removal of light ends and hydrogen as a light ends stream in line 144 and to provide a butene recycle stream in line 146 which is returned to the catalytic distillation column 206 at a point between the feed entry point and the point from which the second side draw stream in line 148 was withdrawn. Although not repeated in FIG. 2, as shown in FIG. 1, a lower catalytic zone 204 may be present in the catalytic distillation column 206 to improve the overall isomerization reaction. A bottom product stream in line 142 comprising the tertiary allyl ether and pentenes is withdrawn from the catalytic distillation column 206. This bottom product stream may be employed in gasoline blending as a high octane component of motor fuel.

A portion of the ethylene stream in line 116 is passed via line 136 to a polymerization zone 207 containing a polymerization catalyst wherein butene-1 in line 132 and ethylene in line 136 polymerized at effective conditions to form a polyethylene product stream in line 134. The polyethylene product stream comprises a linear low density polyethylene.

EXAMPLE

The following example is only used to illustrate the present invention and is not meant to be limiting. The example was developed using engineering design calculations based on pilot plant yields for a methanol-to-olefins operation on methanol.

A $C_4^+$ feedstream separated from the product of a methanol-to-olefins plant for the conversion of methanol at effective conditions over a SAPO-34 catalyst has the composition shown in the following table in the "FEED" column in terms of units per hour. About 515 units of methanol are combined with the feedstream and the feed admixture is passed to a catalytic distillation zone of the present invention. The catalytic distillation zone has an upper catalytic zone containing an etherification catalyst to produce about 1500 units/hour of ethers and a lower catalytic zone containing an isomerization catalyst and a selective hydrogenation catalyst. Approximately 11 units/hour of hydrogen are introduced to the lower catalytic zone by injecting the hydrogen into a liquid side draw stream which is withdrawn from the catalytic distillation zone at a point below the lower catalytic zone and reintroduced to the catalytic distillation zone at a point approximately in the middle or above of the lower catalytic zone. Preferably, the liquid side draw stream is withdrawn at a point where the concentration of butene-2 approaches a maximum which will be at a point between about 8 to about 10 theoretical stages above the bottom of the catalytic distillation zone. The process produced about 4560 units/hour of a bottoms product stream comprising ethers and $C_5$ plus components and about 6100 units/hour of butene-1 product. A butene-1 water wash step to remove about 5 units/hour of methanol is not shown. In this way, the 270 units/hour of butadiene are converted to mixed butenes by the selective hydrogenation catalyst and the mixed butenes are isomerized to produce additional butene-1. Without the selective hydrogenation catalyst in the lower catalytic zone, the butadienes will dimerize to a dimer component and the additional butene-1 will be lost as $C_5$ plus motor fuel.

OVERALL MATERIAL BALANCE FOR THE PRODUCTION OF BUTENE-1
(All Flows in units/hour)

| COMPONENT | FEED | $H_2$ | Methanol | C5+ | Light Ends | Butene-1 |
|---|---|---|---|---|---|---|
| Methanol | | | 515 | | | |
| Hydrogen | | 11 | | | 1 | |
| Isobutane | 50 | | | 50 | | |
| Isobutene | 400 | | | | | 20 |
| Butene-1 | 1700 | | | | | 6080 |
| Butene-2 | 4430 | | | 320 | | |
| Normal-butane | 30 | | | 30 | | |
| Butadiene | 270 | | | | | |
| $C_5$ Saturates | 15 | | | 15 | | |
| Normal pentenes | 1090 | | | 1090 | | |
| Iso-pentenes | 1330 | | | 1330 | | |
| Cyclopentene | 275 | | | 275 | | |
| $C_6$ plus | 610 | | | 610 | | |
| Ethers | | | | 1500 | | |
| TOTAL | 10,200 | | 515 | 4570 | 51 | 6100 |

I claim:

1. A process for the production of butene-1 from a feedstream comprising butene-1, butene-2, isobutylene, and pentenes, comprising the following steps:

a) passing the feedstream and an alcohol stream at effective etherification and separation conditions to a catalytic distillation zone having an upper catalytic zone and a lower catalytic zone and contacting at least a portion of the feedstream in the upper catalytic zone containing an etherification catalyst and therein etherifying the isobutylene with the alcohol stream to produce a tertiary alkyl ether;

b) contacting the remaining portion of the feedstream in the presence of hydrogen at effective isomerization conditions in the lower catalytic zone containing an isomerization catalyst for the isomerization of butene-2 to butene-1 to produce an additional amount of butene-1;

c) recovering a bottoms product stream from the catalytic distillation zone comprising pentenes and tertiary alkyl ether;

d) recovering a top stream from the catalytic distillation zone comprising hydrogen;

e) withdrawing a side draw stream at a point above the upper catalytic zone, said side draw stream comprising the alcohol and butene-1; and, f) passing the side draw stream to an alcohol recovery zone to provide a butene-1 product stream and an oxygenate stream and returning at least a portion of the oxygenate stream to step(a) to provide at least a portion of the alcohol stream.

2. The process of claim 1 further comprising polymerizing the butene-1 product stream with an ethylene stream to produce a polyethylene product.

3. The process of claim 2 wherein the polyethylene product comprises linear low density polyethylene.

4. The process of claim 1 further comprising blending the bottoms product stream with at least one gasoline blending stream selected from the group consisting of a catalytic reformate, a catalytically cracked gasoline, butane, $C_5/C_6$ isomerate, and mixtures thereof to produce a motor fuel.

5. The process of claim 1 wherein the alcohol stream comprises methanol and the tertiary alkyl ether comprises MTBE.

6. The process of claim 1 wherein the feedstream comprises less than 10 vol-% isobutylene.

7. The process of claim 1 wherein the feedstream comprises a $C_4$ plus stream withdrawn from an oxygenate conversion process for the production of olefins over a SAPO catalyst.

8. The process of claim 7 wherein the SAPO catalyst is selected from the group consisting of SAPO-34, SAPO-17, and mixtures thereof.

9. The process of claim 1 wherein the alcohol stream comprises methanol or ethanol.

10. The process of claim 1 further comprising passing the feedstream and the alcohol stream at effective conditions to a pre-etherification reactor containing an etherification catalyst to convert at least a portion of the feedstream and the alcohol prior to passing the feedstream and the alcohol to the catalytic distillation zone.

11. The process of claim 1 further comprising withdrawing a second side draw stream at a point below the lower catalytic zone and passing the second side draw stream at effective conditions in the presence of hydrogen to a butene isomerization zone to produce an isomerized stream and returning the isomerized stream to the catalytic distillation zone.

12. The process of claim 1 wherein the feedstream further comprises butadiene.

13. The process of claim 12 further comprising contacting the butadiene in the lower catalytic zone to produce a dimer component and recovering the dimer component in the bottoms product stream.

14. The process of claim 12 where the lower catalytic zone further comprises a selective hydrogenation catalyst to convert the butadiene to additional butenes and converting the additional butenes to butene-1 in the lower catalytic zone.

15. A process for the production of light olefins comprising ethylene, propylene, and butylene from the conversion of oxygenates, said process comprising the following steps:

a) passing at least a portion of an oxygenate feedstream comprising methanol or ethanol in the presence of a diluent at effective conditions to an oxygenate conversion zone containing a SAPO catalyst to produce a reactor effluent stream comprising said light olefins and passing the reactor effluent stream to a separation zone to produce an ethylene stream, a propylene stream, and a butylene steam;

b) admixing a portion of the oxygenate feedstream with at least a portion of the butylene stream comprising isobutylene, butene-1, and butene-2 to provide a feed admixture and passing the feed admixture at effective conditions to a catalytic distillation column having a top and bottom, said catalytic distillation column having an upper catalytic zone and a lower catalytic zone and contacting at least a portion of the feed admixture in the upper catalytic zone containing an etherification catalyst and therein etherifying the isobutylene with the oxygenate to produce a tertiary alkyl ether;

c) contacting the remaining portion of the feed admixture in the presence of hydrogen at effective conditions in the lower catalytic zone containing an isomerization catalyst for the isomerization of butene-2 to butene-1 to produce an additional amount of butene-1;

d) recovering a bottoms product stream from the catalytic distillation column comprising the tertiary alkyl ether;

e) recovering a top stream from the catalytic distillation column comprising hydrogen;

f) withdrawing a side draw stream at a point above the upper catalytic zone, said side draw stream comprising the oxygenate and butene-1;

g) passing the side draw stream to an oxygenate recovery zone to provide a butene-1 product stream and an oxygenate stream and returning at least a portion of the oxygenate stream to the oxygenate conversion zone.

16. The process of claim 15 further comprising withdrawing a liquid side draw stream comprising butene-2 from the catalytic distillation column at a point below the lower catalytic zone, admixing the liquid side draw stream with hydrogen to provide a hydrogen admixture, and returning the hydrogen admixture to the catalytic distillation column at a point within the lower catalytic zone.

17. The process of claim 16 wherein the liquid side draw stream is withdrawn at a point comprising about 5 to about 15 theoretical trays above the bottom of the catalytic distillation column.

18. The process of claim 15 further comprising passing the feed admixture to a first reaction zone containing an etherification catalyst to at least partially convert a portion of the feed admixture prior to passing the feed admixture to the catalytic distillation column.

19. The process of claim 15 further comprising withdrawing a second side draw stream comprising butene-2 from the catalytic distillation column at a point about 8 to about 12 theoretical stages above the bottom and passing the second side draw stream to an external isomerization zone in the presence of hydrogen to produce an isomerization effluent stream comprising butene-1 and returning the isomerization effluent stream to the catalytic distillation column.

20. The process of claim 19 further comprising passing the isomerization effluent stream to a stripping zone to produce a butene recycle stream depleted in hydrogen and returning the butene recycle stream to the catalytic distillation column.

21. The process of claim 15 further comprising polymerizing a portion of the butene-1 product stream with a portion of the ethylene stream to produce a polyethylene product.

* * * * *